US008268825B2

(12) United States Patent
Dreier et al.

(10) Patent No.: US 8,268,825 B2
(45) Date of Patent: Sep. 18, 2012

(54) METHOD FOR THE TREATMENT OF ANTHRAX INFECTIONS

(75) Inventors: Jurg Dreier, Basel (CH); William Barrow, Stillwater, OK (US); Esther Barrow, Stillwater, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 937 days.

(21) Appl. No.: 11/526,853

(22) Filed: Sep. 25, 2006

(65) Prior Publication Data

US 2010/0305119 A1 Dec. 2, 2010

Related U.S. Application Data

(60) Provisional application No. 60/720,519, filed on Sep. 26, 2005.

(51) Int. Cl.
*A01N 43/58* (2006.01)
*C07D 247/02* (2006.01)
*A61K 31/517* (2006.01)

(52) U.S. Cl. .................. 514/248; 514/234.5; 514/266.4; 514/275; 544/119; 544/237

(58) Field of Classification Search .................. 514/248, 514/234.5, 266.4, 275; 544/119, 237
See application file for complete search history.

(56) References Cited

U.S. PATENT DOCUMENTS 6,114,330 A * 9/2000 Guerry et al. ................. 514/248

FOREIGN PATENT DOCUMENTS

| | | |
|---|---|---|
| EP | 0 966 464 B1 | 5/2003 |
| WO | WO 96/16046 | 5/1996 |
| WO | WO 2004/069255 | 8/2004 |

OTHER PUBLICATIONS

Morissette et al. Advanced Drug Delivery Reviews 2004, 56, 275-300.*

Vippagunta et al., abstract, Vippagunta, Sudha R. "Crystalline Solids." Advanced Drug Delivery Reviews 48(2001): 3-26.*

Stella, Valentino J, Expert Opinion of Therapeutic Patents, Prodrugs as therapeutics, 2004 14(3): 277-280.*

Wolff et al. (Burger's Medicinal Chemistry, 5th Ed., vol. 1, pp. 975-977, 1994).*

Testa, Bernard, Biochemical Pharmacology, Prodrug Research: futile or fertile? 68 (2004) 2097-2106.*

Ettmayer, Peter, Medicinal Chemistry, Lessons Learned from Marketed and Investigational Prodrugs, 47(10) (2004) 2394-2404.*

Inglesby et al. (JAMA, vol. 281 (18), 1999, pp. 1735-1963).*

Barrow, et al., Functional Cloning of *Bacillus anthracis* Dihydrofolate Reductase and Confirmation of Natural Resistance to Trimethoprim, Antimicrobial Agents and Chemotherapy, Jul. 30, 2004, pp. 4643-4649, vol. 48, No. 12, Publisher: American Society for Microbiology, Published in: United States.

Bakici, et al., Antimicrobial Susceptibility of *Bacillus anthracis* in an Endemic Area, Scandinavian Journal of Infectious Diseases, Apr. 30, 2002, pp. 565-566, vol. 34, No. 8, Publisher: Taylor & Francis healthsciences, Published in: Turkey.

Barrow, et al., Functional Cloning of *Bacillus anthracis* Dihydrofolate Reductase and Confirmation of Natural Resistance to Trimethoprim, Antimicrobial Agents and Chemotherapy, Dec. 2004, pp. 4643-4649, vol. 48, No. 12, Publisher: American Society for Microbiology, Published in: United States.

Altboum, et al., Postexposure Prophylaxis against Anthrax: Evaluation of Various Treatment Regimens in Intranasally Infected Guinea Pigs, Infection and Immunity, Nov. 2002, pp. 6231-6241, vol. 70, No. 11, Publisher: American Society for Microbiology, Published in: United States.

Doganay, et al., Antimicrobial Susceptibility of *Bacillus anthracis*, Scandinavian Journal of Infectious Diseases, 1991, pp. 333-335, vol. 23, No. 3, Published in: United States.

* cited by examiner

*Primary Examiner* — Savitha Rao

(74) *Attorney, Agent, or Firm* — Fellers, Snider, Blankenship, Bailey & Tippens, P.C.

(57) ABSTRACT

A method of treating an anthrax infection wherein a compound of formula I (I)

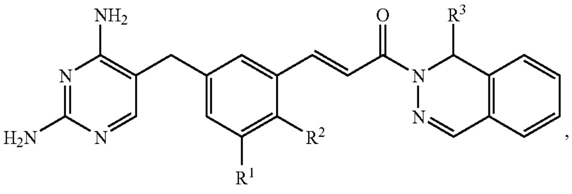

, wherein $R^1$ and $R^2$ represent, independently of one another unsubstituted or specifically substituted $C_{1-4}$alkoxy; and $R^3$ represents hydrogen; cyano; unsubstituted or specifically substituted $C_{1-6}$alkyl; $C_{3-6}$cycloalkyl; $C_{2-6}$alkenyl; $C_{7-18}$bicyclyl; aryl, aryl-$C_{1-4}$alkyl, aryl-Q-$C_{1-4}$alkyl heteroaryl, heterocyclyl or heterocyclyl-$C_{1-6}$alkyl, wherein aryl denotes a mono- or poly-nucleous group with 6 to 14 ring carbon atoms;

heterocyclyl denotes a 4- to 6-membered non-aromatic heterocyclic group comprising 1 to 3, nitrogen, oxygen and/or sulfur atoms; heteroaryl denotes a mono- or polynuclear heteroaromatic group consisting 5- and/or 6-membered rings and comprising 5 to 13 carbon atoms and 1 to 4, nitrogen, oxygen and/or sulfur atoms; and Q means —SO— or —$SO_2$—;

or a pharmaceutically acceptable salt, solvate or hydrate or a prodrug thereof;

is administered to said subject in a quantity effective to inhibit, suppress, or expel an anthrax infection in said subject.

20 Claims, No Drawings

METHOD FOR THE TREATMENT OF ANTHRAX INFECTIONS

CROSS REFERENCE TO RELATED APPLICATION

This application claims the benefit of U.S. Provisional Application No. 60/720,519, filed with the Patent and Trademark Office on Sep. 26, 2005, which application is hereby incorporated by reference.

STATEMENT REGARDING FEDERALLY SPONSORED RESEARCH OR DEVELOPMENT

The Government of the United States of America has certain rights in this invention pursuant to Grant No. 5 R21 AI055643-02 awarded by the National Institutes of Health through the National Institute Allergy and Infectious Diseases.

BACKGROUND OF THE INVENTION

The present invention relates to the treatment of anthrax infections and to the use of certain 2,4-diaminopyrimidine compounds for the manufacture of medicaments for said treatment.

Anthrax is a highly infectious disease that normally affects animals, for example goats, cattle, sheep or horses, but which can be transmitted to humans by contact with infected animals, infected animal products or *Bacillus anthracis* spores.

The transmitter of anthrax is a bacterium called *Bacillus anthracis*, an encapsulated Gram-positive, nonmotile, aerobic, spore-forming bacterium. Its spores resist destruction and remain viable in the soil and in animal products for years, even for decades.

Humans are usually infected through the skin or from eating meat contaminated with anthrax resulting in cutaneous or gastrointestinal forms of anthrax infections. Substantial danger may also come from the spores of anthrax, which, once inhaled, can result in a disease in the lungs referred to as pulmonary anthrax or also as woolsorter's disease and which is usually fatal.

Nowadays anthrax is rare in humans in the developed industrial countries, however, it still occurs largely in less developed countries not sufficiently preventing exposure of humans to infected animals and their products.

Furthermore, there is great concern about anthrax as an agent of biological warfare and bioterrorism.

Today, antibiotics are given to unvaccinated individuals exposed to inhalation anthrax. Penicillin, tetracyclines and fluoroquinolones are known to be effective if administered within about 24 hours. Ciprofloxin is approved by the FDA for a postexposure treatment of inhalational anthrax.

Nevertheless, there is an ongoing great interest in finding new antibacterial drugs for said purpose, for example, as an alternative for fighting strains of *Bacillus anthracis* which are or become resistant against the present antibiotics.

SUMMARY OF THE INVENTION

Trimethoprim (TMP), a compound belonging to the structural class of the 2,4-diaminopyrimidines, is an antibacterial drug well-known in the art as a dihydrofolate reductase (DHFR) inhibitor. DHFR is a proven antibacterial target, and DHFR inhibitors are used to treat various infections. TMP is frequently used in combination with sulfamethoxazole (SMZ), which acts on a different target enzyme in folic acid synthesis than TMP. Dogonay & Aydin, Scand J Infect Dis 23: 333-335, 1991 indicated that TMP-SMZ exhibits a certain activity against anthrax, later reports, however, showed that clinical isolates of *Bacillus anthracis* were resistant to TMP-SMZ in vitro (Bakici et al. Scand J Infect Dis 34: 564-566, 2002). Furthermore it was also shown that the *Bacillus anthracis* Sterne strain was resistant to TMP, with minimal inhibitory concentration (MIC) values between 2048 and 4096 μg/ml (Barrow et al. Antimicrob Agents Chemother 48 (12): 4643-4649, 2004) and that TMP-SMZ was inactive as a postexposure prophylactic against anthrax in an animal model (Aitboum et al. Infect Immun 70 (11): 6231-6241, 2002). The very low activity of TMP on DHFR purified from *Bacillus anthracis* (concentration at which the enzyme is inhibited by 50% ($IC_{50}$)=77.2 μM) has been reported as the molecular reason for the observed resistance of *Bacillus anthracis* against TMP (Barrow et al. Antimicrob Agents Chemother 48 (12): 4643-4649, 2004).

WO 2004/069255 describes the use of certain 2,4-diaminoquinazoline or 2,4-diamino-5,6,7,8-tetrahydroquinazoline derivatives as inhibitors for bacterial DHFR, and as agents against bacterial infections, mentioning also *Bacillus anthracis* among a long list of bacteria which could in principle be a possible target for said compounds. The reference does however not provide any data whatsoever showing activity against *Bacillus anthracis* or an inhibition of DHFR isolated thereof.

It has now been found that 2,4-Diaminopyrimidine compounds of formula I (I)

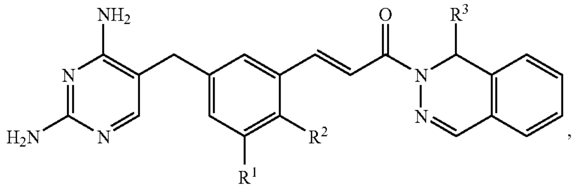

wherein $R^1$, $R^2$, $R^3$ have the meaning described in more detail herein below, exhibit pronounced efficacy in inhibiting DHFR of *Bacillus anthracis* strains. This is particularly surprising in view of the fact that TMP, notwithstanding its structural relationship to the compounds of formula I has been found ineffective against *Bacillus anthracis* as indicated above.

The present invention therefore relates to a method of treating an anthrax infection in a subject in need of such treatment wherein a compound of formula I (I)

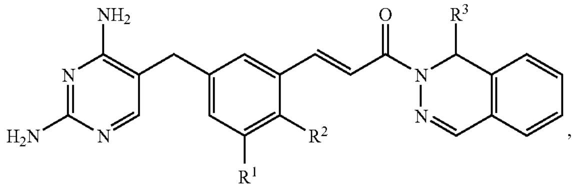

wherein $R^1$ and $R^2$ represent, independently of one another:

$C_{1-4}$alkoxy which may be unsubstituted or substituted with amino, mono- or di($C_{1-4}$alkyl)amino, morpholino, piperidino, piperazino, hydroxy, halogen, cyano, thiocyanato, sulfonyl, methylsulfanyl, oxo, carboxy, carbamino, carbalkoxy, $C_{1-4}$alkoxy, morpholinoalkoxy or piperidinoalkoxy; and $R^3$ represents:

hydrogen;

cyano;

$C_{1-6}$alkyl or $C_{3-6}$cycloalkyl, which both may be unsubstituted or substituted with amino, mono- or di($C_{1-4}$alkyl)amino, morpholino, piperidino, piperazino, hydroxy, halogen, cyano, thiocyanato, sulfonyl, methylsulfanyl, oxo, carbamino, carbalkoxy, $C_{1-4}$alkoxy, morpholinoalkoxy or piperidinoalkoxy;

$C_{2-6}$alkenyl, which may be unsubstituted or substituted with cyano, acryloyl or heterocyclyl;

$C_{7-18}$bicyclyl;

aryl, aryl-$C_{1-4}$alkyl, aryl-Q-$C_{1-4}$alkyl, heteroaryl, heterocyclyl or heterocyclyl-$C_{1-6}$alkyl, each of which may be unsubstituted or substituted with phenyl, $C_{1-4}$alkyl, fluoro- or polyfluoro$C_{1-4}$alkyl, $C_{3-6}$cycloalkyl, hydroxy, cyano, thiocyanato, amino, mono- or di($C_{1-4}$alkyl)amino, hydroxy-$C_{1-4}$alkyl, which may be esterified with an amino acid or sulfuric acid, halogen, $C_{1-4}$alkoxy, $C_{1-4}$alkoxycarbonyl; carbamoyl, mono- or di($C_{1-4}$alkyl)carbamoyl, $C_{1-4}$alkylsulfanyl, $C_{1-4}$alkylsulfonyl, sulfamoyl, N-mono- or di($C_{1-4}$alkyl)sulfamoyl, heterocyclyl, or heterocyclyl-$C_{1-4}$alkyl; aryl-$C_{1-4}$alkyl;

wherein furthermore aryl denotes a mono- or poly-nucleous group with 6 to 14 ring carbon atoms heterocyclyl denotes a 4- to 6-membered non-aromatic heterocyclic group comprising 1 to 3, nitrogen, oxygen and/or sulfur atoms;

heteroaryl denotes a mono- or polynuclear heteroaromatic group consisting of 5- and/or 6-membered rings and comprising 5 to 13 carbon atoms and 1 to 4 nitrogen, oxygen and/or sulfur atoms; and Q means —SO— or —$SO_2$—;

a pharmaceutically acceptable salt, solvate or hydrate or a prodrug thereof;

is administered to said subject in a quantity effective to inhibit, suppress, or expel an anthrax infection in said subject.

In another aspect the present invention relates to the use of a compound of formula I as described herein above for the manufacture of a medicament for the treatment of an anthrax infection.

A better understanding of the present invention, its several aspects, and its objects and advantages will become apparent to those skilled in the art from the following detailed description, taken in conjunction with the attached drawings, wherein there is shown and described the preferred embodiment of the invention, simply by way of illustration of the best mode contemplated for carrying out the invention.

DETAILED DESCRIPTION OF THE PREFERRED EMBODIMENTS

The compounds of formula I and their general usefulness for the treatment of bacterial infections by virtue of their DHFR inhibiting efficacy, in particular for the treatment of infections caused by resistant pneumococci and opportunistic pathogens such as *Pneumocystis carinii* are known from EP-A-0 966 464.

For the purposes of this application the term compound of formula I includes all epimers, enantiomers and diastereomers and mixtures thereof. The term $C_{1-4}$alkoxy as meant with regard to formula I includes straight or branched chain types, e.g. methoxy, ethoxy, n-propoxy, isopropoxy, n-butyloxy, 2-methyl-propoxy, isobutyloxy and tert-butoxy, for example.

$C_{1-6}$alkyl where used in this application means preferably $C_{1-4}$alkyl. $C_{1-6}$alkyl or $C_{1-4}$alkyl groups in formula I may be straight or branched chain groups, and include groups like methyl, ethyl, n-propyl, isopropyl, n-butyl, isobutyl, tert.-butyl, n-pentyl and n-hexyl.

Examples of $C_{1-8}$cycloalkyl are e.g. cyclopropyl, cyclobutyl, cyclopentyl, cyclohexyl or cycloheptyl.

The above groups may be substituted by one, two or more substituents, typical substituents being selected from amino, mono- or di($C_{1-4}$alkyl)amino, morpholino, piperidino, piperazino, hydroxy, halogen, cyano, thiocyanato, sulfonyl, methylsulfanyl, oxo, carbamino, carbalkoxy, $C_{1-4}$alkoxy, morpholinoalkoxy or piperidinoalkoxy. Methoxymethyl, hydroxymethyl, hydroxybutyl, dihydroxybutyl, 2-oxo-propyl, 3-oxo-propyl, perfluorohexyl, cyclopentanonyl, cyclohexanonyl and the like are examples of such substituted alkyl and alkoxy groups. Preferably the $C_{1-4}$alkoxy, $C_{1-6}$alkyl or $C_{1-8}$cycloalkyl groups of the compounds of formula I are unsubstituted.

$C_{2-6}$alkenyl is meant herein to embrace unsaturated hydrocarbon residues containing a double bond, in particular residues such as vinyl, allyl, butenyl and the like. The alkenyl chain is optionally substituted by one or more substituents, such as, for example, cyano acryloyl, or heterocyclyl, as defined herein.

Examples for preferred bicyclyl groups are adamantyl or bicyclo[2.2.1]hept-2-endo- and/or 2-exo-yl.

Preferred examples of suitable aryl groups are phenyl, naphthyl, anthryl and phenanthryl, which can be substituted by one or more substituents. Suitable substituents for either mentioned aryl groups are e.g. phenyl; $C_{1-6}$alkyl (e.g. methyl); substituted $C_{1-6}$alkyl as defined above (e.g. trifluoromethyl, pentafluoro ethyl); $C_{3-6}$cycloalkyl (e.g. cyclopropyl); hydroxy; cyano; thiocyanato; amino; hydroxyalkyl, optionally esterified with amino acids or sulphuric acid (such as, for example, 2-amino-propionic acid ester or 2-amino-5-guanidino-pentanoic acid ester); halogen (e.g. chlorine); $C_{1-4}$alkoxy (e.g. methoxy, n-butoxy); substituted $C_{1-4}$alkoxy as described above; $C_{1-4}$ alkoxycarbonyl (e.g. methoxycarbonyl); di($C_{1-4}$alkyl)amino (e.g. dimethylamino, diethylamino); carbamoyl, mono- or di-$C_{1-4}$alkylcarbamoyl; $C_{1-4}$ alkylsulphanoyl, (e.g. methylsulphanyl); $C_{1-4}$alkylsulphonyl, (e.g. methanesulphonyl); sulphamoyl, N-mono- or di-$C_{1-4}$ alkylsulphamoyl; heterocyclyl, or with heterocyclyl-$C_{1-6}$ alkyl. Additionally, aryl can be substituted by two vicinal alkoxy groups which form a fused ring, such as, for example, 2,3-dihydro-benzo[1,4]dioxin-6-yl and benzo[1,3]dioxin-5-yl. Preferably the aryl groups are unsubstituted.

Examples for the meaning of the term “heterocyclyl” include groups derived from e.g. lactones, lactames, cyclic ketals (such as, for example, 2-dimethyl-1,3-dioxolan-yl), cyclic acetals (e.g. 1,3, dioxolan-2-yl or 1,3,-dioxan-2-yl). More specific examples of heterocyclyl groups are morpholin-4-yl, 4-methyl-piperazin-1-yl, imidazol-1-yl, thiazolyl and [1,2,4]triazol-1-yl, dithianyl, tetrahydropyranyl. The heterocyclic rings can be substituted with substituents described above for the aryl and lower alkyl groups. Such substituents are especially lower alkyl, lower alkoxy, hydroxy, amino, hydroxyalkyl, aminoalkyl or oxo. Pyrrolidinone, methylpyrrolidinone and the like are examples of particularly preferred substituted heterocyclic rings.

The term “heterocyclyl-$C_{1-6}$alkyl” embraces in the scope of the present invention heterocyclic rings which are linked via an $C_{1-6}$alkyl residue. Preferred heterocyclyl-$C_{1-6}$alkyl units are e.g morpholin-4-ylmethyl, 4-methyl-piperazin-1-ylmethyl, imidazol-1-ylmethyl and [1,2,4]triazol-1-ylmethyl, dioxolan-4-ylethyl, pyrrolidinylmethyl, pyperidinylmethyl and the like. The heterocyclyl and $C_{1-6}$alkyl groups can each be unsubstituted or substituted as provided for above.

The term "heteroaryl" denotes residues like, for example, furyl, pyranyl, thienyl, pyrrolyl, pyrazolyl, imidazolyl, triazolyl, tetrazolyl, oxazolyl, oxadiazolyl, isoxazolyl, thiazolyl, isothiazolyl, pyridyl, pyridazinyl, pyrimidinyl, pyrazinyl, triazinyl. These groups can also be linked with a fused ring, preferably a phenyl ring. Examples of such linked rings are, for example, benzopyranyl, benzofuranyl, indolyl and quinolinyl. The heteroaryl groups can be substituted, for example with substituents as described above for the aryl and $C_{1-6}$alkyl groups. Additionally, heteroaryl can be substituted by two vicinal alkoxy groups which form a fused ring, such as, for example, [1,3]dioxolo[4,5-b]pyridin-6-yl.

As used herein, halide or halogen refer to chloride or chlorine, fluoride or fluorine, bromide or bromine, and iodide or iodine.

In formula I the group $R^1$ is preferably methoxy; $R^2$ is preferably hydroxy, $C_{1-4}$alkoxy such as e.g. methoxy or ethoxy; or $C_{1-4}$alkoxy substituted by $C_{1-4}$alkoxy, such as e.g. methoxymethoxy; $C_{1-4}$alkoxy substituted by heterocyclyl such as e.g. morpholin-4-yl-ethoxy or $C_{1-4}$ alkoxy substituted by $C_{1-4}$alkoxycarbonyl-$C_{1-6}$alkyl, preferably methoxycarbonylmethyl Preferred $C_{1-6}$alkyl groups $R^3$ include the following groups: methyl; ethyl; propyl; n-butyl, 3-methyl-butyl and tert.-butyl, in particular butyl and more particular ethyl. Preferred substituents for the $C_{1-6}$alkyl residue $R^3$ include the following substituents: hydroxy such as e.g. hydroxypropyl, hydroxybutyl, 3,4-dihydroxybutyl; methylsulfanyl such as e.g. methylsulfanylmethyl; fluoro such as e.g. tridecafluorhexyl; carbamoyloxy such as e.g. carbamoyloxy-butyl, carbamoyloxy-propyl; thiocyanato such as e.g. thiocyanatobutyl; —$SO_4H$ such as e.g. sulfatobutyl; or heterocyclyl such as e.g. [1.3]dioxolan-2-yl-ethyl, [1.3]dioxolan-4-yl-ethyl; heterocyclylcarbonyloxy such as e.g. morpholinylcarbonyloxy-butyl.

Preferred substituents for the alkenyl-residue $R^3$ include cyano such as e.g. cyanobutenyl; or acryloyl such as e.g. acryloylbutenyl.

Preferred $C_{3-6}$cycloalkyl groups $R^3$ include cyclopropyl, cyclobutyl, and in particular cyclopentyl and cyclohexyl. Said cycloalkyl groups may be substituted e.g. by an oxo group but are most preferably unsubstituted.

Preferred heterocyclyl- or substituted heterocyclyl-residues $R^3$ include: dithian-2-yl or tetrahydropyran-2-on-1-yl.

Examples for the group "aryl-Q-$C_{1-6}$alkyl" include phenylsulfonylmethyl or phenylsulfinylmethyl.

The preferred aryl group $R^3$ is phenyl. Said phenyl residue can be mono, di- or tri-substituted by $C_{1-6}$alkyl such as e.g. methyl, ethyl, butyl, tert-butyl; substituted $C_{1-6}$alkyl such as e.g. hydroxymethyl, hydroxy-ethyl, methoxymethyl, trifluormethyl; halogen, preferably fluoro; methylsulfanyl; dimethylamino; dimethylamino sulfonyl; cyano; hydroxy; $C_{1-4}$alkoxy such as e.g. methoxy; substituted $C_{1-4}$alkoxy such as e.g. hydroxyethoxy, trifluoromethoxy, 1-ethoxy-ethoxy, 2-ethoxy-ethoxy; $C_{1-4}$alkoxy-carbonyl such as e.g. tert.-butoxy carbonyl; heteroaryl such as e.g. pyrrol-1-yl; heterocyclyl-$C_{1-6}$alkyl such as e.g. 4-methyl-piperazin-1-yl-methyl, 4-morpholin-4-yl-methyl.

Preferred heteroaryl groups $R^3$ include pyridyl, pyrimidinyl, thiophen-2-yl, 5,6-dihydro-4H-pyran-2-yl, furan-2-yl, thiazol-2-yl, [1,3]dioxolo[4,5-b]pyridin-6-yl.

The heteroaryl groups $R^3$ can be mono-, di- or tri-substituted, independently of one another e.g. by $C_{1-4}$alkyl such as e.g. methyl, ethyl; substituted $C_{1-4}$alkyl such as e.g. hydroxymethyl, hydroxy-1-methyl-ethyl; halogen, preferably fluoro, chloro, bromo; $C_{1-4}$alkoxy such as e.g. methoxy; substituted $C_{1-4}$alkoxy such as e.g. methoxy-ethoxy, methoxy-ethoxy-ethoxy, hydroxy-ethoxy, hydroxypropoxy, 2-morpholin-4-yl-ethoxy, dimethylamino-ethoxy; benzyloxy; dimethylamino; amino-carbonyl; tert.-butyl-amino-carbonyl; heterocyclyl like morpholin-4-yl.

Particularly preferred for use in the treatment of anthrax infections or for use in the manufacture of medicaments for the treatment of such infections corresponding to the purposes of the present invention are compounds of the above formula I wherein $R^1$ and $R^2$ represent, independently of one another $C_{1-4}$alkoxy or N-morpholino-$C_{1-4}$alkoxy, in particular wherein $R^1$ is $C_{1-4}$alkoxy, preferably methoxy, and $R^2$ N-morpholino-$C_{1-4}$alkoxy, preferably N-morpholino-ethoxy.

Even more preferred for use in the treatment of anthrax are the compounds of the above formula I, wherein $R^1$ and $R^2$ are both $C_{1-4}$alkoxy and most preferably methoxy. Regarding the group $R^3$ such compounds of formula I are especially preferred wherein $R^3$ stands for $C_{1-6}$alkyl or $C_{3-8}$cycloalkyl, which both may be unsubstituted or substituted with halogen; or aryl, aryl-$C_{1-4}$alkyl, heteroaryl, heterocyclyl or heterocyclyl-$C_{1-6}$alkyl, in particular wherein $R^3$ stands for unsubstituted $C_{1-6}$alkyl, preferably $C_{3-4}$alkyl; or $C_{3-6}$cycloalkyl, preferably $C_{5-6}$cycloalkyl, or most preferable for aryl, in particular phenyl.

Presently most preferred for the treatment of anthrax are the compounds of formula I wherein $R^1$ and $R^2$ are both methoxy and $R^3$ is either propyl or phenyl.

Those compounds of formula I in which $R^3$ is different from hydrogen can be present in racemic form or as the R- or S-enantiomer or any mixture of said enantiomers.

Specific examples of preferred compounds of formula I useful as inhibitors of DHFR of *Bacillus anthracis* and accordingly for the treatment of infections caused by strains of said *Bacillus* and for manufacture of medicaments for such treatment are as follows:

A: (E)-(RS)-3-[5-(2,4-Diamino-pyrimidin-5-ylmethyl)-2,3-dimethoxy-phenyl]-1-(1-phenyl-1H-phthalazin-2-yl)-propenone;

B: (E)-(RS)-3-[5-(2,4-Diamino-pyrimidin-5-ylmethyl)-2,3-dimethoxy-phenyl]-1-(1-propyl-1H-phthalazin-2-yl)-propenone;

C: (E)-(RS)-3-[5-(2,4-Diamino-pyrimidin-5-ylmethyl)-2,3-dimethoxy-phenyl]-1-(1-butyl-1H-phthalazin-2-yl)-propenone;

D: (E)-(RS)-3-{5-(2,4-Diamino-pyrimidin-5-ylmethyl)-2,3-dimethoxy-phenyl}-1-(1-cyclopentyl-1H-phthalazin-2-yl)-propenone;

E: (E)-(RS)-3-{5-(2,4-Diamino-pyrimidin-5-ylmethyl)-2,3-dimethoxy-phenyl}-1-(1-cyclohexyl-1H-phthalazin-2-yl)-propenone;

F: (E)-(RS)-3-{5-(2,4-Diamino-pyrimidin-5-ylmethyl)-3-methoxy-2-(2-morpholin-4-yl-ethoxy-phenyl}-1-(1-phenyl-1H-phthalazin-2-yl)-propenone;

as well as the pharmaceutically acceptable salts of these compounds.

The compounds of formula I can for instance be prepared according to the methods described in EP-A-0 966 464, which virtually exemplifies most of the compounds of formula I specifically mentioned herein, or in an equivalent or analogous way.

The compounds of formula I can also be used for the treatment of anthrax in form of pharmaceutically acceptable acid addition salts with organic and inorganic acids. Examples of acid addition salts of compounds of formula I are salts with mineral acids, for example hydrohalic acids, such as hydrochloric acid, hydrogen bromide and hydrogen iodide, sulphuric acid, nitric acid, phosphoric acid and the like, salts with organic sulphonic acids, for example with alkyl- and aryl-sulphonic acids such as methanesulphonic, p-toluene-sulphonic, benzene-sulphonic acid and the like, as well as salts with organic carboxylic acids, for example with acetic acid, tartaric acid, maleic acid, citric acid, benzoic acid, salicylic acid, ascorbic acid and the like. Such salts can be prepared in a way known in the art, e.g. as described in EP-A-0 966 464.

The formation of solvates of the compounds of formula I including hydrates may vary depending on the compound and the solvate. In general, solvates are formed by dissolving the compound in the appropriate solvent and isolating the solvate by cooling or using an antisolvent. The solvate is typically dried or azeotrope under ambient conditions.

The term "prodrug" as meant in this application, refers to any compound which is metabolized either by the subject to which is administered or by the anthrax bacilli with which the subject is infected. The design of prodrugs is described, for example, in "Design of Prodrugs", edited by Hans Bundgaard, 1985 Elsevier Science Publishers B.V.

The term "treating an anthrax infection" is understood as obtaining results beneficial for the infected subject, in particular beneficial clinical results. Such results include, in particular, that an anthrax infection is either inhibited in said subject, suppressed or expelled or at least alleviated. "Inhibiting an anthrax infection" means that a subject which cannot reasonably avoid to get in contact with *Bacillus anthracis*, has a significantly reduced risk to develop an anthrax infection as compared to the risk of a subject under the same conditions who has not got a treatment with a compound of formula I. "Suppressing an anthrax infection" means, in particular, that a subject definitely having been in contact with *Bacillus anthracis* or spores thereof, e.g. by inhaling such *Bacillus* or spores, has a significantly reduced risk, when compared with an untreated subject under the same conditions, of developing dangerous or even life-threatening symptoms of an anthrax infection, if the treatment with compounds of formula I commences after said contact of the subject with the bacilli or spores. "expelling an anthrax infection" means that a subject already having one or more symptoms of a manifest anthrax infection has a significantly increased chance for overcoming that infection, preferably without substantial aftermath.

A subject is preferably a human, but may also be an animal susceptible to anthrax infection, in particular a ruminant such as a horse, a cow, a sheep or a goat.

The inhibition of dihydrofolate reductase of *Bacillus anthracis* is taken as a measurement of the activity of the compounds of formula I against anthrax infections.

For determining the inhibiting activity of the compounds measurements of $IC_{50}$ and MIC are performed.

1) $IC_{50}$ Measurement:

DHFR catalyses the conversion of dihydrofolate into tetrahydrofolate and concomitantly oxidizes the cofactor NADPH into NADP. These conversions cause a decrease of absorbance at 340 nm, which can be measured to follow the enzyme reaction. A detailed description of the assay is published (Barrow et al. Antimicrob Agents Chemother 48 (12): 4643-4649, 2004).

$IC_{50}$ Determination (Enzyme Inhibition Assay)

In more detail, the inhibition of both human and *Bacillus anthracis* DHFR is determined with the following procedure.

For drug inhibition assays a solution of each drug is prepared at a concentration of 1.024 mg/ml in dimethylsulfoxide (DMSO). Dilutions of this drug concentration are further prepared in DMSO (1:3, 1:10, 1:30, 1:100, 1:300, 1:1,000, 1:3,000, 1:30,000). The nM concentration of drug in these dilutions is calculated based on the molecular weight. Ten microliters of each drug dilution is tested in an inhibition reaction.

The reaction mixture (1.0 ml) contains (1) 100 μl of 10× assay buffer (500 mM potassium phosphate buffer, 10 mM ethylenediaminetetraacetic acid (EDTA), pH 7.0: concentration in reaction mixture is 50 mM potassium phosphate buffer-1 mM EDTA, pH 7.0), (2) 100 μl 2-mercaptoethanol (100 mM: concentration in reaction mixture is 10 mM), (3) 680 μl water, (4) 50 μl reduced nicotinamide adenine dinucleotide phosphate (NADPH) (2 mM: concentration in reaction mixture is 0.1 mM), (5) 10 μl enzyme (containing 0.66 μg in 125 mM potassium phosphate buffer, 2.5 mM EDTA, 0.1% bovine serum albumin, pH7), (6) 10 μl of drug dilution.

This mixture is heated for 3 minutes in a 30° C. water bath, followed by the addition of (7) 50 μl dihydrofolate (2 mM: concentration in the reaction mixture is 0.1 mM). The solution is read for 3 minutes at 340 nm in a spectrophotometer, and the activity is measured as the decrease in the optical density at 340 nm (O.D. 340) over 3 minutes at 30° C.

This is compared with a control reaction in which all conditions and reagents are the same with the exception that 10 μl of DMSO (no drug) is used.

The percent inhibition in each reaction is calculated using the following formula:

$$\% \text{ inhibition}=100-((\Delta \text{ O.D. 340 inhibition reaction}/\Delta \text{ O.D. 340 control reaction})\times 100)$$

An $IC_{50}$ value is generated by using KC Junior software (Bio-Tek Instruments, Inc.) which plots $\log_{10}$ of the drug concentration versus % Inhibition.

Each reported $IC_{50}$ is the average of two or more determinations.

2) MIC Determination:

MIC values are determined in 96-well microtiter plates prepared according to the NCCLS broth microdilution reference method (i.e. alamarBlue™ microdilution broth assay). Details of the method are described in Barrow et al. Antimicrob Agents Chemother 48 (12): 4643-4649, 2004.

In more detail, the minimal inhibitory concentration (MIC) of compounds against *Bacillus anthracis* Steme is determined using an alamarBlue™ microdilution broth assay. 96-well microtiter panels of test compounds and control antibiotics are prepared according to the NCCLS broth microdilution reference method in cation-adjusted Mueller-Hinton broth (BD) containing 10% alamarBlue™ (CAMHB/10% aB) dye reagent (Biosource Int. Ca), (NCCLS, January 2003, "Methods for dilution antimicrobial susceptibility tests for bacteria that grow aerobically"; approved standard-6*th* edition, M7-A6, vol. 23, No. 2).

MIC Drug Plates Preparation:

Screening MIC drug plates contain test compounds at four concentrations (10-fold dilutions) in CAMHB/10% aB: 0.128, 1.28, 12.8 and 128 μg/ml. These drug concentrations are prepared from −20° C. frozen stocks of each drug solubilized in sterile DMSO.

Quality control (QC) antibiotics are prepared from −80° C. aqueous stocks at 2-fold dilutions in CAMHB/10% aB.

Doxycycline is prepared at 0.25, 0.5 and 1.0 μg/ml.

TMP/SMZ is prepared at 1.25/4.75, 0.5/9.5, 1.0/19, and 2/38 μg/ml.

Sterility and growth control wells contain CAMHB/10% aB while solvent control wells contain CAMHB/10% aB with appropriate concentrations of sterile DMSO.

Once screening assays are completed, MIC drug plates are prepared with test drugs at 2-fold dilutions in CAMHB/10% aB. Drug concentrations vary from drug to drug based on MIC screening results.

All wells in the microtiter panels contain 100 μl.

Test compounds are plated in triplicates, while sterility controls, solvent controls and QC drugs are plated in duplicate.

*Escherichia coli*, ATCC 25922, is used to validate doxycycline performance.

TMP/SMZ is used against *Enterococcus faecalis* ATCC 29212 to validate the medium for antifolate testing.

Doxycycline is used as a QC drug against *Bacillus anthracis* Sterne at 0.25, 0.5, and 1.0 μg/ml.

These drugs and their concentrations are used based on CLSI interpretive standards for *Bacillus anthracis, Escherichia coli*, and *Enterococcus faecalis*. (CLSI, M100-15, Vol. 25 No. 1).

Inoculum Preparation and Plate Infection:

*Bacillus anthracis* Sterne is subcultured twice on Trypticase soy agar (TSA) plates containing 5% sheep blood (Hardy Diagnostics, Ca). Cultures are incubated at 37° C. overnight. Growth is transferred to 5 ml sterile saline and suspended to a turbidity of a 0.5 McFarland standard (NCCLS, January 2003, "Methods for dilution antimicrobial susceptibility tests for bacteria that grow aerobically"; approved standard-6$^{th}$ edition, M7-A6, vol. 23, No. 2). A 1:20 dilution of this solution is prepared in CAMHB/10% aB.

All wells with the exception of sterility and color control wells are inoculated with 10 μl of the inoculum. Microdilution panels are placed in a gas-diffusable polypropylene bag and incubated at 37° C. in ambient air for 16 hours.

The colony forming units (cfu) in the final inoculum is verified by inoculating appropriate dilutions on TSA blood agar and determining the number of colonies after overnight incubation. The final inoculum is $5\times10^5$ cfu/ml or $5\times10^4$ cfu/100 μl as recommended by CLSI.

Following incubation, results were read visually and spectrophotometrically in a microplate reader programmed to subtract the absorbance at 600 nm from that at 570 nm. The MIC is reported as the lowest drug concentration yielding a differential absorbance of zero or less (i.e., color remains blue).

MIC values are compared to acceptable limits for QC strains to validate drug performance. All quality control tests must fall within acceptable ranges (*Escherichia coli*, doxycycline 0.5-2.0 μg/mL, *Bacillus anthracis*, doxycycline≦1.0 μg/mL, *Enterococcus faecalis* TMP/SMZ≦0.5/9.5 μg/mL) for results to be considered valid.

The following Table contains the mentioned values determined for representative members of the class of compounds defined by formula I and determined in the above tests. The $IC_{50}$ values (nM) for DHFR of *Bacillus anthracis* and for human DHFR are given, furthermore the MIC values of the respective compounds for *Bacillus anthracis*. The corresponding values for TMP are also given for comparison.

| Compound of formula I | $IC_{50}$ (nM) *B. anthracis* DHFR | $IC_{50}$ (nM) human DHFR | MIC *B. anthracis* (ug/ml) |
|---|---|---|---|
| Trimethoprim | $7.7 \times 10^4$ | $1.6 \times 10^6$ | >2000 |
| 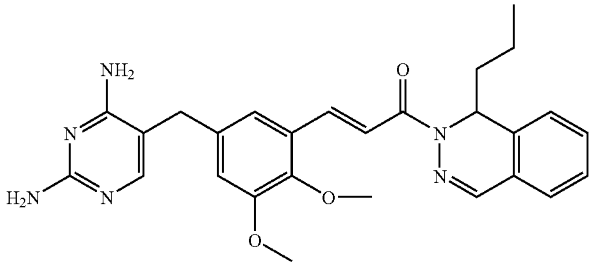 | 54 | 110000 | 13 |
| 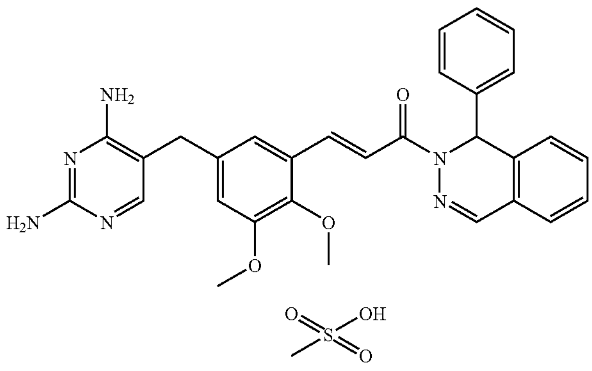 | 46 | >16000 | 26 |

-continued

| Compound of formula I | $IC_{50}$ (nM) *B. anthracis* DHFR | $IC_{50}$ (nM) human DHFR | MIC *B. anthracis* (ug/ml) |
|---|---|---|---|
| 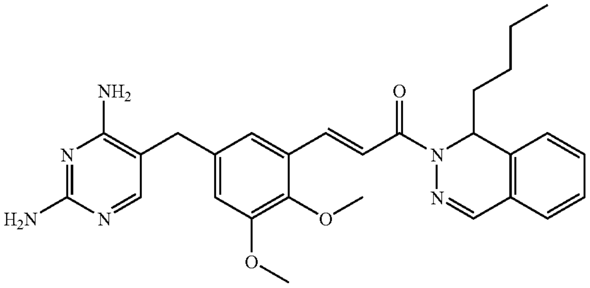 | 170 | >20000 | ≦13 |
| 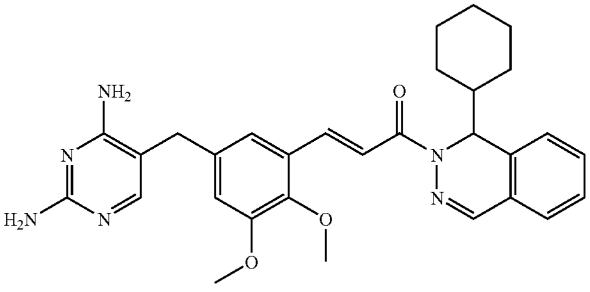 | 260 | >19000 | ≦13 |
| 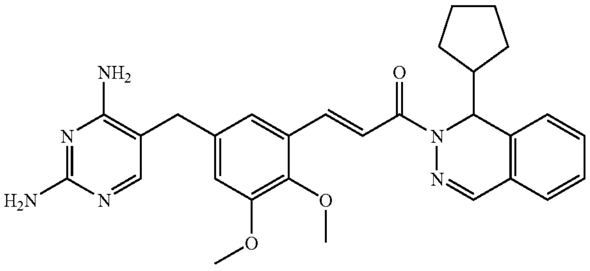 | 200 | >21000 | ≦26 |
| 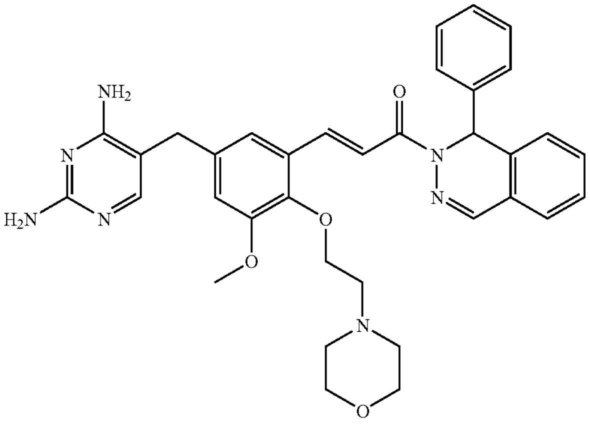 | 170 | >16000 | ≦32 |

A preferred embodiment of the present invention is a method as described above, wherein a compound of formula I is administered which exhibits in vitro an $IC_{50}$ value for human DHFR which is at least 70 times, more preferably at least 100 times, most preferably at least 250 times as high as that for DHFR of *Bacillus anthracis*.

A further object of the present invention is a method for inhibiting DHFR of *Bacillus anthracis* in vitro, wherein a compound of formula I is applied to an assay for determining the inhibition of DHFR of *Bacillus anthracis*, and a respective method further comprising the selection of a compound of formula I as a candidate for in vivo and/or clinical tests based on the efficacy in inhibiting DHFR of *Bacillus anthracis* in vitro found for said compound.

The compounds of formula I and the salts, solvates, hydrates or prodrugs thereof are preferably formulated into pharmaceutical compositions for administration to human subjects in a form suitable for administration in vivo. Making the pharmaceutical preparations can be effected in a manner which will be familiar to any person skilled in the art by bringing the substances in accordance with the invention, optionally in combination with other therapeutically valuable substances, into a galenical administration form together with suitable, non-toxic, inert therapeutically compatible solid or liquid carrier materials and, if desired, the usual pharmaceutical adjuvants.

Both inorganic and organic carrier materials are suitable as such carrier materials. Thus, for example, lactose, corn starch or derivatives thereof, talc, stearic acid or its salts can be used as carriers for tablets, coated tablets, dragees and hard gelatin capsules. Suitable carriers for soft gelatin capsules are, for example, vegetable oils, waxes, fats and semi-solid and liquid polyols (depending on the nature of the active ingredient no carriers are, however, required in the case of soft gelatin capsules). Suitable carrier materials for the production of solutions and syrups are, for example, water, polyols, sucrose, invert sugar and glucose. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols.

The usual preservatives, solubilizers, stabilizers, wetting agents, emulsifiers, sweeteners, colorants, flavorants, salts for varying the osmotic pressure, buffers, masking agents and antioxidants come into consideration as pharmaceutical adjuvants. For parenteral administration the compounds of formula I and, respectively, their salts are preferably provided as lyophilizates or dry powders for dilution with usual carriers such as water or isotonic saline.

In accordance with the method of the invention, compounds of formula I or salts, solvates, hydrates or prodrugs thereof may be administered to a subject in a variety of forms depending on the selected route of administration, as will be understood by those skilled in the art. The compounds or compositions may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

The compounds of Formula I or salts, solvates, hydrates or prodrugs thereof may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the compound may be incorporated with excipient and used in the form of ingestible tablets, buccal tablets, troches, capsules, elixirs, suspensions, syrups, wafers, and the like.

Compounds of Formula I or salts, solvates, hydrates or prodrugs thereof may also be administered parenterally or intraperitoneally. Solutions of the compound can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations.

Pharmaceutical compositions suitable for injectable use include sterile aqueous solutions or dispersion and sterile powders for the extemporaneous preparation of sterile injectable solutions or dispersions. In all cases the form must be sterile and must be fluid to the extent that easy syringability exists.

Compositions may also be formulated as aerosols, drops, gels, cremes and powders. Aerosol formulations typically comprise a solution or fine suspension of the active substance in a physiologically acceptable aqueous or non-aqueous solvent and are usually presented in single or multidose quantities in sterile form in a sealed container. Such formulations may be used with a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine.

Compositions for rectal administration are conveniently in the form of suppositories containing a conventional suppository base such as cocoa butter.

The dosage of the compounds of Formula I or salts, solvates, hydrates or prodrugs thereof can vary depending on many factors such as the pharmacodynamic properties, of the compound, the mode of administration, the age, health and weight of the recipient, the nature and extent of the symptoms, the frequency of the treatment and the type of concurrent treatment, if any, and the clearance rate of the compound. One of skill in the art can determine the appropriate dosage based on the above factors. The compounds may be administered initially in a suitable dosage that may be adjusted as required, depending on the clinical response. A daily dosage of about 0.2 g to about 2 g, preferably 0.5 to 2 g of a compound of formula I in accordance with the invention comes into consideration for adults.

Compounds of Formula I or salts, solvates, hydrates or prodrugs thereof, may be used alone or in combination with other types of DHFR inhibitors or with other agents that treat anthrax infections like for example quinolones, rifampin, tetracycline, vancomycin, imipenem, meropenem, chloramphenicol, clindamycin or macrolides.

While the invention has been described with a certain degree of particularity, it is understood that the invention is not limited to the embodiment(s) set for herein for purposes of exemplification, but is to be limited only by the scope of the attached claim or claims, including the full range of equivalency to which each element thereof is entitled.

What is claimed is:

1. A method of treating an anthrax infection in a subject in need of such treatment wherein a compound of formula (I)

(I)

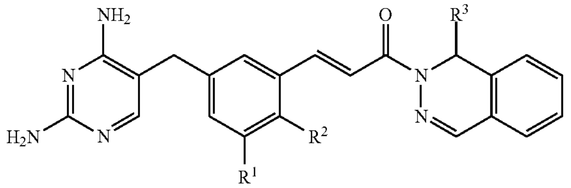

wherein

R1 and R2 represent, independently of one another: unsubstituted $C_{1-4}$ alkoxy or morpholino; and $R_3$ represents:

$C_{1-6}$ alkyl or $C_{3-6}$ cycloalkyl, which both may be unsubstituted or substituted with halogen;

unsubstituted $C_{2-6}$ alkenyl;

aryl which may be unsubstituted or substituted with, $C_{1-4}$ alkyl, halogen, $C_{1-4}$ alkoxy, or substituted $C_{1-4}$ alkoxy, or a pharmaceutically acceptable salt thereof;

is administered to said subject in a quantity effective to inhibit, suppress, or expel an anthrax infection in said subject.

2. A method according to claim 1, wherein said compound is administered for the treatment of an anthrax infection of the respiratory tract.

3. A method according to claim 1, wherein said compound is administered for the treatment of cutaneous anthrax infections.

4. A method according to claim 1, wherein said compound is administered for the treatment of an anthrax infection of the gastrointestinal tract.

5. A method according to claim 1 wherein said compound of formula (I) exhibits in vitro an $IC_{50}$ value for human DHFR which is at least 70 times, more preferably at least 100 times, most preferably at least 250 times as high as that for DHFR of *Bacillus anthracis.*

6. A method for inhibiting DHFR of *Bacillus anthracis* in vitro, comprising determining the inhibition of DHFR of *Bacillus anthracis* by using, in an assay, a compound of Formula (I):

(I)

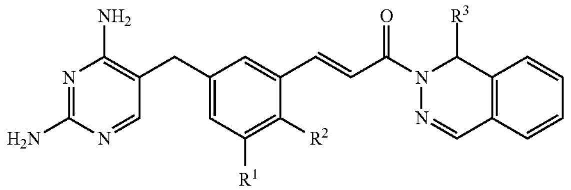

wherein

R1 and R2 represent, independently of one another:

unsubstituted C1-4 alkoxy or morpholino and R3 represents:

C1-6 alkyl or C3-6 cycloalkyl, which both may be unsubstituted or substituted with halogen, unsubstituted C2-6 alkenyl; or aryl, which may be unsubstituted or substituted with phenyl, C1-4 alkyl, halogen, or C1-4 alkoxy.

7. A method according to claim 6, further comprising selecting said compound of formula (I) as a candidate for in vivo and/or clinical tests based on the efficacy in inhibiting DHFR of *Bacillus anthracis* in vitro found for said compound.

8. The method of claim 1, wherein said unsubstituted $C_{1-4}$ alkoxy is methoxy or ethoxy.

9. The method of claim 1, wherein said $C_{1-6}$ alkyl is a substituted or unsubstituted $C_{3-5}$ alkyl.

10. The method of claim 9, wherein said unsubstituted $C_{3-5}$ alkyl is selected from the group consisting of propyl, isopropyl, butyl, isobutyl, and 1-ethylpropyl.

11. The method of claim 9, wherein said substituted $C_{3-5}$ alkyl is substituted propyl.

12. The method of claim 9, wherein said substituted $C_{3-5}$ alkyl is substituted with halogen.

13. The method of claim 9, wherein said halogen is fluorine.

14. The method of claim 1, wherein said $C_{3-6}$ cycloalkyl is a $C_{5-6}$ cycloalkyl selected from cyclopentyl and cyclohexyl.

15. The method of claim 1, wherein said unsubstituted $C_{2-6}$ alkenyl is a $C_4$ alkenyl.

16. The method of claim 1, wherein said aryl is a substituted or unsubstituted 6-carbon ring aryl.

17. The method of claim 16, wherein said substituted 6-carbon ring aryl is substituted with one or more methyl groups, halogen, $C_{1-4}$ alkoxy , or trifluoromethoxy.

18. The method of claim 17, wherein said halogen is fluorine.

19. The method of claim 17, wherein said $C_{1-4}$ alkoxy is methoxy.

20. The method of claim 11, wherein said substituted $C_{1-4}$ alkoxy is trifluoromethoxy.

* * * * *